United States Patent [19]

Melbin

[11] Patent Number: 5,104,402
[45] Date of Patent: Apr. 14, 1992

[54] PROSTHETIC VESSELS FOR STRESS AT VASCULAR GRAFT ANASTOMOSES

[75] Inventor: Julius Melbin, Wallingford, Pa.

[73] Assignee: Trustees of the University of Pennsylvania, Philadelphia, Pa.

[21] Appl. No.: 496,343

[22] Filed: Mar. 20, 1990

Related U.S. Application Data

[62] Division of Ser. No. 198,787, May 25, 1988, Pat. No. 4,938,740.

[51] Int. Cl.$^5$ .............................................. A61F 2/06
[52] U.S. Cl. ......................................... 623/1; 623/12
[58] Field of Search ................................ 623/1, 11, 12

[56] References Cited

U.S. PATENT DOCUMENTS 3,155,095 11/1964 Brown ................................ 128/334
4,441,215 4/1984 Kaster ...................................... 623/1

Primary Examiner—David J. Isabella
Assistant Examiner—Debra S. Brittingham
Attorney, Agent, or Firm—Woodcock Washburn Kurtz Mackiewicz & Norris

[57] ABSTRACT

Prosthetic vessels having improved resistance to occlusion by tissue reaction upon implantation by reducing transmural stresses are also disclosed. Prostheses having elliptical cross-sections governed by the maximum strain expected in the natural vessel and possessing a higher bulk compliance than previous designs are provided. Additionally, novel methods are presented for implanting improved prostheses by using angled bias cuts to produce an elliptical cross-section at each end of the natural vessel section receiving the prosthesis. In accordance with preferred embodiments, vessels are provided where the cross-sectional geometry is approximated by the equations:

$$a = r_0[1 + 2\epsilon(2+\epsilon)]^{\frac{1}{2}}$$

and $$b = r_0.$$

6 Claims, 2 Drawing Sheets

PROSTHETIC VESSELS FOR STRESS AT VASCULAR GRAFT ANASTOMOSES

This is a division of application Ser. No. 198,787, filed May 25, 1988, now U.S. Pat. No. 4,938,740, issued on July 3, 1990.

This invention relates to improvements in small vessel prostheses which reduce both static and dynamic stresses resulting from differences in elastic properties between the prosthesis and the vessel to which it is anastomosed. Such improvements reduce the likelihood of occlusion. Further, this invention is directed to methods for implanting reduced stress prostheses.

BACKGROUND OF THE INVENTION

For a variety of reasons, it is often medically desirable to replace a section of a blood vessel, either a vein or an artery, with a prosthesis rather than using a viable tissue graft. A difficulty frequently encountered in the replacement of a natural vessel section with a prosthesis is that, despite successful surgical implantation, the prosthesis occludes and thereby fails in its function. This problem is particularly troublesome with what can be described as small vessel prostheses, particularly those intended to replace or repair small arterial sections. The resulting blockage in the artery (lumen occlusion) usually occurs at the sites of the anastomoses and, if the prosthetic material is adequately blood compatible, is primarily due to tissue reactions such as endothelial, smooth muscle cell, or fibroblast proliferation, rather than clot formation. There is evidence to suggest that mismatch at the suture line between the elastic properties of the host vessel and the prosthesis is a primary contributor to mechanisms underlying these reactions.

All vessel materials manifest several important viscoelastic properties, the determination of the significance of these properties is dependent upon the application, loading conditions, loading frequencies and other variables. The nonlinear elastic modulus of most biomaterials dominates their mechanical behavior in a vessel application; the variation in this property between natural and prosthetic materials can span orders of magnitude. If a vessel is sutured to a prosthesis with an identical unloaded geometry, the relatively smaller load bearing surface of the sutures tends to impart significant stress concentrations at the interface, particularly if the prosthesis has a different elastic modulus. For example, a small artery with a lumen diameter on the order of 2 mm (0.08 inches), developing a peak strain on the order of 0.1, can develop peak azimuthal wall stresses on the order of $10^5 - 10^6$ dyne/cm$^2$ (1.45 – 14.5 lb/in$^2$). If a natural vessel is sutured to a prosthesis with an elastic modulus one order of magnitude greater, the resulting stress at a suture can easily achieve a value two orders of magnitude greater than the normal peak azimuthal stress. This increased stress burden brought about by the mismatch can cause severe tissue reactions which may lead to the failure of the implant.

As might be expected, reactions common to viable tissue under stress, e.g., fibroblast and muscle cell proliferation or hypertrophy, collagen synthesis, venous graft "arterialization", etc., can occur in the vessel. For example, research has demonstrated that smooth muscle cell proliferation occurs as a direct consequence of cyclic tensile stress. See, Leung, et al. "A New In Vitro System for Studying Cell Response to Mechanical Stimulation", Experimental Cell Research, Vol. 109, pp. 285–89, (1977), incorporated herein by reference.

If all other factors remain constant, as lumen diameters increase, wall stress increases in direct proportion to the lumen radius. However, since the cross-sectional area increases in proportion to the square of the radius, the occlusive problem is progressively diminished with increasing lumen diameter, despite similar reactions at the site of the anastomosis. Therefore, although stress reduction is important in all vessel prosthetics, the problem is particularly acute in the range of lumen diameters below about four millimeters. See, Proceedings, Workshop on Blood, Transport Phenomena, and Surfaces, National Institutes of Health Publication No. 86-2726 (1986) (hereinafter "NIH Workshop"), incorporated herein by reference.

Previous attempts to solve the problem of stress-induced tissue reactions have largely concentrated on the material surface properties, as well as the mismatch of elastic properties between the vessel and the prosthesis—in other words a search for a "perfect material" to be used as a prosthesis. Progress has been made by selecting materials and constructing prostheses for particular site-specific applications. Other research continues. In particular, studies of material properties such as porosity and compliance, as well as studies of the mechanical properties of diseased arteries have been identified as promising areas of reasearch. See, NIH Workshop at 77-78.

Although many areas of research hold promise, there is currently a need within the medical profession to have the capability to implant reliable prostheses in patients with diseased or damaged vessels. As reflected by the current state of the art, there exists at this time no general solution to this problem since no material has been found to have the requisite surface and mechanical properties while being biomedically acceptable as a prosthesis. There is, therefore, a long-felt but unsolved need for a small diameter prosthetic vessel having improved elastic properties to eliminate or substantially reduce the stress imparted at the anastomosis.

OBJECTS OF THE INVENTION

It is an object of this invention to provide a class of small vessel prostheses which will reduce the occlusions resulting from reactions to cyclic stresses generated at anastomoses.

It is another object of this invention to provide small vessel prostheses which minimize the stress loading on the natural vessel generally without regard to the material utilized.

It is yet another object of this invention to provide a class of small vessel prostheses which place no excessive stress upon natural vessels over any expected range of transmural loading experienced following implantation.

It is a further object of this invention to provide methods for selecting the geometry of small vessel prostheses such that a bulk compliance is achieved which results in no untoward stress loading on the natural vessel.

It is still a further object of this invention to provide methods for grafting prostheses made in accordance with this invention to small vessels in a manner that does not develop untoward static or dynamic stresses at the anastomoses.

SUMMARY OF THE INVENTION

In accordance with this invention, a class of small vessel prostheses are provided which minimize vessel stresses, without primary regard to material property mismatch, by providing an optimal prosthetic geometry. Bulk compliance, as applied to the protheses of this invention, is defined as an aggregate of material and geometric properties. Every material possesses quantifiable mechanical properties such as its modulus of elasticity, modulus of rigidity, Poisson's ratio, etc. from which material behavior under loading can be determined. Further, any given geometry has identifiable structural properties defined by its section modulus, which is derived from the cross-sectional moment of inertia for a particular geometry. It has been determined that the compliance attributable to the properties possessed by a particular material within a defined loading range can be relegated to a second order consideration if the prosthetic geometry is carefully controlled. Thus, it is now possible to achieve a bulk compliance such that, with essentially no regard to the material chosen, no excessive stress loading is imparted to the natural vessel. The material chosen need only be biologically compatible, that is, it must be capable of being anastomosed to a living vessel without being rejected or otherwise causing unacceptable thrombus to occur. Prostheses made in accordance with the present invention can be formed from polyethylene terephthalate (Dacron), polytetraflouroethylene (Teflon) or any other biologically compatible material, the material choice now largely a matter of surface property considerations and physician preference. The method and prostheses of the present invention are useful with any biologically compatible material, known or discovered in the future, for use in either human or veterinary applications.

In accordance with this invention, the interfacial stresses developed in small vessel prostheses are greatly reduced by sectioning the vessel to be anastomosed on a prescribed bias such that an elliptic section is developed. The prosthetic vessel is constructed such that in its unloaded state it possesses substantially the same elliptic cross-section at its anastomotic planes as that selected for the exposed end of the natural vessel. The cross-sectional area of an elliptic vessel increases substantially upon transmural loading while exhibiting relatively little extensional deformation, which may be defined as alteration in perimeter length between unloaded and loaded states. Therefore, an elliptical geometry is chosen to minimize the stresses imparted upon the natural vessel over the expected range of vessel deformation.

When the natural and prosthetic vessels are anastomosed, the bias cuts creating the elliptic cross-sections result in a vessel structure possessing a local directional flow change on the order of 30°–40°. Since the prosthesis' distortions operate primarily in an inextensional deformation mode, the natural vessel is not constrained or stressed significantly. The result is a significant reduction in tissue stress and as a consequence, tissue reactions, which are believed to be a primary cause of lumen occlusion.

Accordingly, this invention satisfies the need for a class of small vessel prostheses which reduces the occurrence of occlusions resulting primarily from tissue reactions to cyclic stress. The small vessel prostheses of this invention utilize novel geometries which avoid transferring excessive stresses to the natural vessel over the expected range of transmural loading, generally independently of the materials used. Additionally, this invention is directed to methods for selecting prosthetic geometry such that the bulk compliance achieved significantly reduces the stress placed upon the natural vessel. Although the prostheses of the present invention possess the same useful properties without regard to size, they represent a particularly useful solution to the previously described long felt need to prevent occlusion in vessels with a lumen diameter of less than four millimeters.

This invention also provides methods which minimize the stresses generated at the anastomoses when preparing natural vessels to be anastomosed to prostheses made in accordance with this invention.

The features and advantages of the present invention will be more fully understood by reference to the drawings.

BRIEF DESCRIPTION OF THE DRAWINGS

FIG. 1A shows an elevation view of a portion of a cylindrical vessel 10 which has been prepared for the grafting of a prosthesis made in accordance with the present invention by making bias cuts 12 and 14 at an angle $\alpha$, which is the acute included angle between a cylindrical axis 16 and the plane of bias cuts 12 and 14. Shown in FIG. 5, is the circular cross-section of vessel 10 with lumen 15 and radius "r". FIG. 6 illustrates the elliptical section formed at the anastomotic plane of the natural vessel by bias cuts 12 and 14, having a major axis 2a and a minor axis 2b.

Figure 1A:
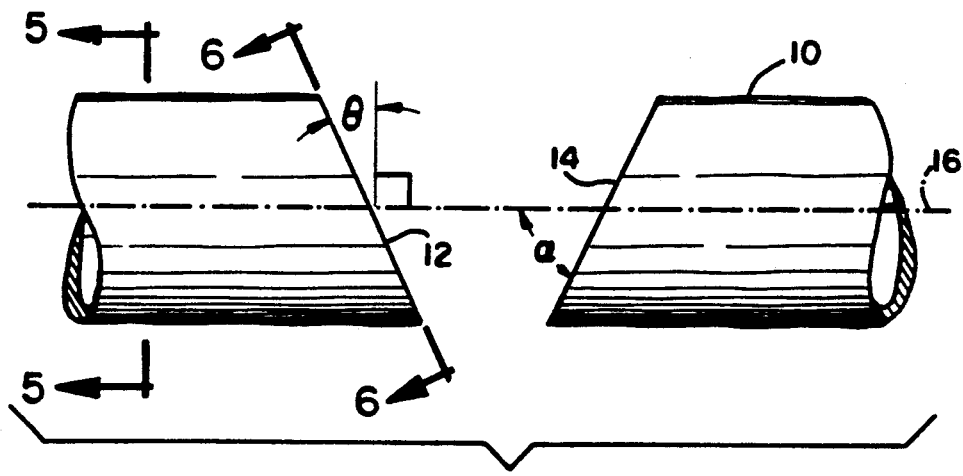
FIG. 1A shows an elevation view of a portion of a cylindrical vessel.
Figure 1B:
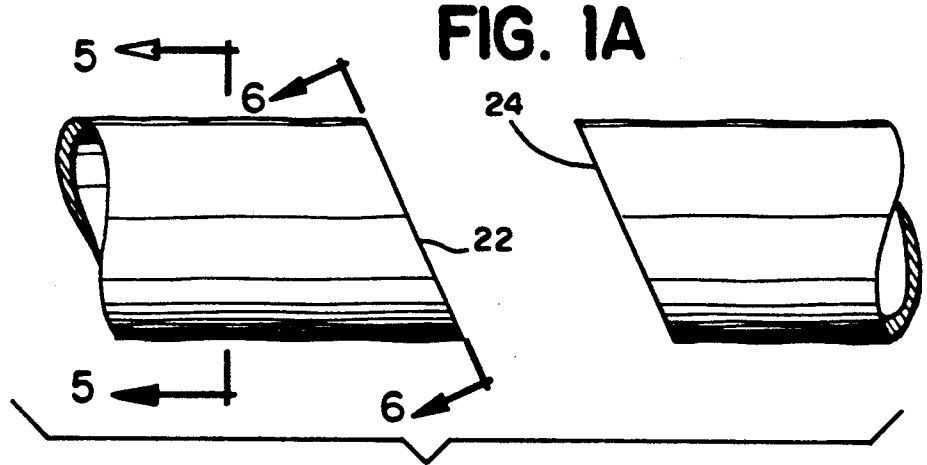
FIG. 1B shows an alternative embodiment of the vessel shown in FIG. 1A.

An alternative embodiment of the present invention is pictured in FIG. 1B. As shown, the bias cuts 22 and 24 are made at angle $\alpha$ as in FIG. 1A, however, the cuts are now made generally parallel to each other. The resulting elliptic shape formed at the anastomotic planes is substantially the elliptic shape shown in FIG. 6.

Figure 2:
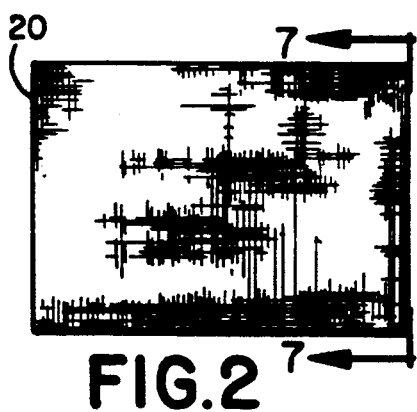
FIG. 2 shows an elevation view of a prosthesis having an approximately elliptical cross section at each end.
Figure 5:
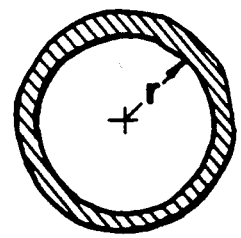
FIG. 5 shows a circular cross section of a vessel with radius "r".
Figure 6:
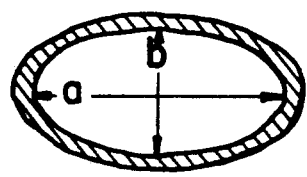
FIG. 6 shows the elliptical section formed at the anastomotic plane of the natural vessel by bias cuts.
Figure 7:
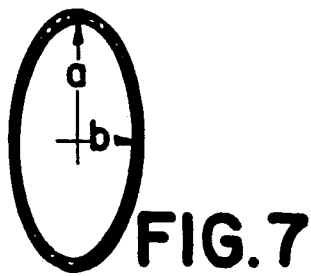
FIG. 7 shows the elliptical cross-section of FIG. 2.

FIG. 2 is an elevation view of a prosthesis 20 having an approximately elliptical cross-section at each end. It will be appreciated that the central portion of the prosthesis may not necessarily be of elliptic cross-section. FIG. 7 illustrates the elliptical cross-section of FIG. 2, having major and minor axes approximately equal to those of the vessel 10 at the anastomotic planes, as illustrated in FIG. 6.

Figure 3:
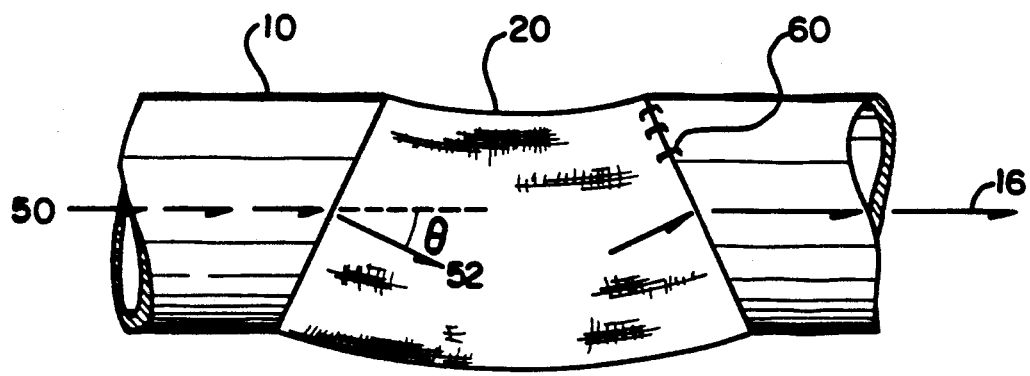
FIG. 3 depicts a completed graft utilizing a vessel prepared as in FIG. 1A and a prosthesis of the invention.

FIG. 3 depicts a completed graft utilizing a vessel 10 prepared as shown in FIG. 1A and prosthesis 20 of the present invention. The prosthesis 20 has been affixed to the vessel 10 at anastomoses 30 and 40, using sutures 60 or other means for joining the vessel 10 and prosthesis 20. Also shown are flow vectors 50 and 52 illustrating the flow path change through the prosthesis 20. The path change may be described by the angle $\theta$, which is defined as the included acute angle between a first flow vector 50 flowing parallel to the cylindrical axis 16 of the vessel 20, and a second flow vector 52 flowing perpendicular to the plane of the bias cuts 12 and 14. The angle $\theta$ can be further described by the equation $\theta = (90° - \alpha)$ as can be seen by comparing FIGS. 1 and 3.

Figure 4:
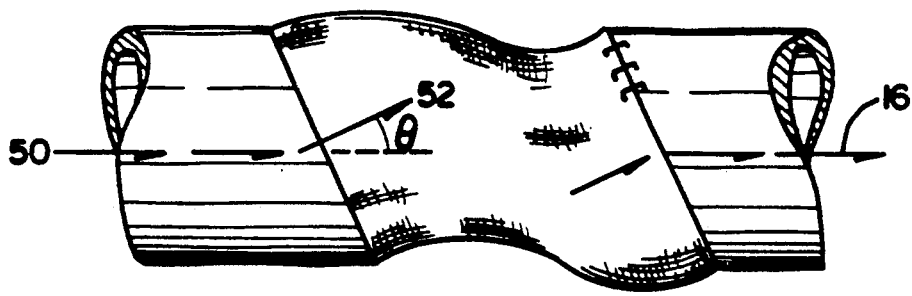
FIG. 4 depicts an alternative embodiment of a completed graft using a vessel prepared as in FIG. 1B and a prosthesis of the invention.

FIG. 4 depicts an alternative embodiment of a completed graft utilizing a vessel 10 prepared as shown in FIG. 1B and a prosthesis 20 of the present invention. Due to the difference in the relationship between the bias cuts, it can be seen that the prosthesis assumes a somewhat different shape. The embodiment of FIG. 4 possesses the same properties which result in stress reduction at the sites of the anastomoses. The prosthesis 20 has been affixed to the vessel 10 at anastomoses 30 and 40, using sutures 60 or other means for joining the vessel 10 and prosthesis 20. Also shown are flow vectors 50 and 52 illustrating the flow path change through the prosthesis 20. It will be noted that although the actual flow path differs from that shown in FIG. 3, the path change may still be described by the angle $\theta$ which is defined in the same manner as described above.

Figure 8:
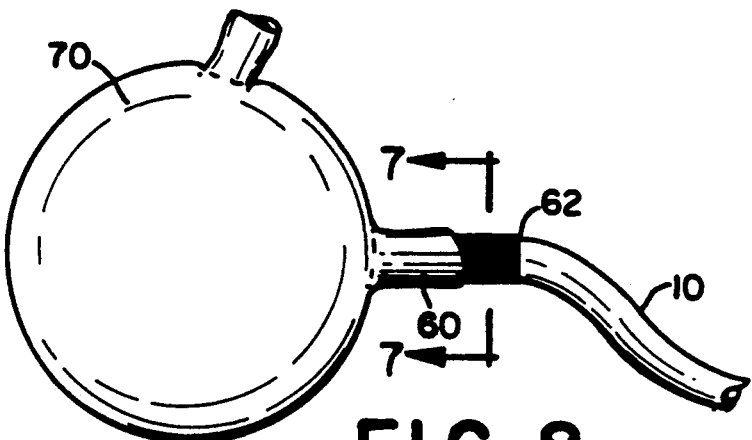
FIG. 8 depicts an embodiment wherein the prosthesis and method of the present invention are applied to one end of an extension which is attached to a medical device.

FIG. 8 depicts an embodiment wherein the prosthesis and method of the present invention are applied to one end of an extension 60 which is attached to a medical device 70. This device can be an infusion apparatus, a drug pump, an artificial organ or any other apparatus attached to any natural vessel. One of ordinary skill in the art will appreciate that the distal end 62 of the extension should be approximately elliptical in cross-section in accordance with the present invention. The portion of the extension 60 which lies between the distal end 62 and the medical device 70 need not be an elliptical cross-section, in the same manner as the central portion of the prosthesis shown in FIG. 2.

One of ordinary skill in the art will be able to construct prostheses in accordance with the present invention in view of the following exemplary procedure, giving due consideration to the constraints discussed.

When constructing small vessel prostheses having novel configurations which, in accordance with the present invention, reduce stress at the anastomoses, the following constraints generally govern the geometry of such designs:

1. In the unloaded state or under minimal transmural loading, the circular vessel should not appreciably distort the prosthesis. This constraint generally requires that, given an approximately circular vessel, the unloaded lumen radius $r_0$ should approximate the minor semi-axis of the elliptic section of the prosthesis.

2. In the fully stressed state an initially elliptic prosthesis should not constrain or place significant stresses upon the natural vessel. This constraint requires that prosthetic distortion at the anastomoses operate primarily in the inextensional deformation mode, that is, the alteration in perimeter length between unloaded and loaded states should be minimized.

In accordance with a preferred embodiment of the present invention, an elliptical cross-section is chosen because of its high degree of geometric compliance. Although other geometries also exhibit this desirable property, since vessels generally exhibit roughly circular cross-sections, an analysis of the geometric and physical characteristics of such an interface may be undertaken without undue complexity.

If an elliptical or near elliptical shape is assumed for the prosthesis, the cross-section may be described by defining major and minor axes, $2a$ and $2b$. In order to minimize strain upon the unloaded vessel, the minor semi-axis, "b", should be approximately equal to the unloaded vessel radius, $r_0$. In order to completely define the geometry of the prosthesis, the length of the major axis $2a$ should also be determined. When a major axis length is determined, the first constraint is essentially complied with by selecting an appropriate bias angle for the natural vessel, such that the anastomotic plane is approximately equal to the prosthetic geometry. In other words, with respect to the first constraint, the natural vessel should be cut at an angle such that the exposed end of the natural vessel has an elliptical shape approximately the same as the unloaded shape of the prosthesis being used.

It is well known that vessels carrying blood or other body fluids tend to undergo expansion upon loading. The pressure of the fluid causes a relatively uniform expansion of the perimeter of the vessel which may be expressed as a strain, that is, the difference between the expanded and unexpanded vessel perimeter length divided by the unexpanded perimeter length. This measure of strain is unitless or is sometimes expressed as inches/inch (mm/mm). When fully loaded, a relatively circular natural vessel expands slightly to a diameter $r_1$ and circumference $l_1$. If the incremental increase in radius is $\Delta r$, the radial expansion can be described as:

$$r_1 = (r_0 + \Delta r)$$

and:

$$l_1 = 2\pi r_1$$

By minimizing the alteration in perimeter length of the prosthesis at the anastomotic plane between loaded and unloaded states, the second constraint governing the design of prostheses made in accordance with this invention may generally be complied with. This can be accomplished by setting the circumference of the prosthesis, $l_p$, to be approximately equal to $l_1$. Thus, when the vessel distends, the prosthesis places only minimal restraint upon it. Therefore, it is seen that:

if $$l_p \approx l_1$$

then $$2\pi \left[ \frac{a^2 + b^2}{2} \right]^{\frac{1}{2}} \approx 2\pi r_1$$

Substituting $r_0$ for "b", $(r_0 + \Delta r)$ for $r_1$, and solving for $a^2$ yields:

$$a^2 = r_0^2 + 4r_0\Delta r + 2\Delta r^2 \qquad (1)$$

Strain, $\epsilon$, may be defined as change in length divided by total length:

$$\epsilon = \frac{r_1 - r_0}{r_0} = \frac{\Delta r}{r_0}$$

And therefore:

$$\Delta r = r_0 \epsilon$$

Substituting $r_0\epsilon$ for $\Delta_r$ in equation (1) above and solving for "a" results in an expression for the relationship between ellipse geometry and vessel strain:

$$a = r_0[1 + 2\epsilon(2+\epsilon)]^{\frac{1}{2}} \quad (2)$$

This expression shows that the initial eccentricity is independent of absolute vessel size but dependent upon expected maximum vessel azimuthal strain. The strain expected in a particular vessel is usually known within the art; for example, in small diameter blood vessels, the expected strain is on the order of 0.1, with an expected maximum of 0.2. The strain expected within a particular type of vessel may be easily determined experimentally if a value is not already known.

The preceding considerations allow the geometry of an elliptical vessel possessing the characteristics of minimizing the stresses imparted on the natural vessel to be defined in accordance with this invention. For a given vessel with radius $r_0$ and a given strain $\epsilon$, the major semi-axis, "a", of the elliptical prosthesis may now be calculated, and the minor semi-axis "b" can be set approximately equal to $r_0$.

An elliptical prosthesis designed to conform to the above constraints is preferably grafted to a natural vessel in a manner which takes full advantage of the increased compliance resulting from its novel geometry. Therefore, a method of grafting a prosthesis made in accordance with the present invention is provided. This method has the further advantage of providing a greater perimeter length over which sutures or other means of forming the anastomosis may be spaced, thus further reducing stress at each suture.

In order to implant a prosthesis made in accordance with the present invention, it is necessary to cut the natural vessel on a bias to produce an elliptical cross-section approximately the same shape as the elliptical cross-section of the prosthesis when the natural vessel is viewed perpendicular to the plane of the bias cut. If $\alpha$ is defined as the acute included angle between the cylindrical axis of the vessel and the anastomotic plane of the natural vessel, and "a" is the major semi-axis of the elliptical cross-section of the prosthesis, and since $r_0$ is the radial distance between the cylindrical axis and the perimeter of the lumen, the geometry may be described by the following equation:

$$\sin \alpha = \frac{r_0}{a} = \frac{1}{[1 + 2\epsilon(2+\epsilon)]^{\frac{1}{2}}}$$

Solving for $\alpha$:

$$\alpha = \sin^{-1}\left[\frac{1}{1 + 2\epsilon(2+\epsilon)}\right]^{\frac{1}{2}}$$

From this equation it is seen that the angle of the bias is not dependent upon the relative vessel size, but upon the expected strain value. For example, an expected strain value $\epsilon \approx 0.1$ dictates that the bias cut angle $\alpha$ is about 57°.

Since the natural vessel is cut on a bias and joined to a prosthesis whose ends are generally perpendicular to its immediate central axis, the resulting implant section induces a change in the flow path of the contained fluid. For the above example, the change in direction of flow is about 33°. A change in flow direction may introduce flow related factors that may affect regional transport, clotting, local endothelial cell thickening, etc. In general these problems are expected to be relatively insignificant in comparison to the stress-induced problems which are though to be the primary cause of occlusion in other small vessel prostheses.

A prothesis made in accordance with this invention is implanted after making the prescribed bias cuts in the natural vessel by suturing each end of the elliptical prosthesis to the prepared elliptical faces of the natural vessel. The present invention contemplates other methods of forming the anastomoses, and is not limited to sutures. Thus, adhesives, staples, and other means for fastening are included within the scope of this invention. The prosthesis takes a generally arc-shaped path between the two bias cuts, inducing the change in direction of flow discussed, but as one skilled in the art will appreciate, the completed prosthesis places no excessive stress upon the natural vessel/prosthesis interface, even upon full loading. Alternatively, the bias cuts may be made in a manner such that they are generally parallel; thus the prosthesis will take on a slightly "S"-shaped configuration. This configuration also provides stress reduction at the anastomotic planes.

The application of the article and method of the present invention is not limited to the replacement of small arterial sections. Using the concepts discussed above, one of ordinary skill in the art will be able to construct extensions or interfaces to medical devices, which may have one or more inputs and outputs, so as to take advantage of the stress-reduction benefits of the present invention. The term medical device is meant to encompass any object which is surgically attached to a patient or animal by anastomoses. Such devices may include but are not limited to medichemiant infusion devices, blood pumping apparatus, artificial hearts, artificial endocrine organs, filtration devices, dialysis devices or any connection to any medical apparatus which is anastomosed to a patient or animal subject.

While certain embodiments have been set forth with particularity, persons of ordinary skill in the art will recognize that other embodiments may be possible employing the spirit of this invention.

What is claimed is:

1. An implantable prosthetic vessel for attachment to a generally elliptical opening of a natural vessel, the prosthetic vessel having improved resistance to occlusion upon implantation, comprising:

an elongated tubular portion, formed from a biologically compatible material, having at least one end having a generally elliptical cross-section at an anastomotic plane perpendicular to a central axis of said tubular portion, the elliptical cross-section having approximately the same dimensions as the elliptical opening to which the prosthetic vessel is attached thereby reducing both static and dynamic stresses between the prosthetic vessel and the natural vessel.

2. The prosthetic vessel of claim 1, wherein said biologically compatible material is polytetrafluoroethylene.

3. The prosthetic vessel of claim 1, wherein said biologically compatible material is polyethylene terephthalate.

4. The prosthetic vessel of claim 1, wherein the distance across the lesser of the geometric axes of said elliptical cross-section is less than about 4 mm (0.16 inches).

5. The prosthetic vessel of claim 1, wherein said generally elliptical cross-section is approximately defined by the equations:

$$a = r_0[1 + 2\epsilon(2+\epsilon)]^{\frac{1}{2}}$$

and $$b = r_0$$

Where "a" is the major semi-axis of said generally elliptic cross-section, "b" is the minor semi-axis of said generally elliptic cross-section, "$r_0$" is the unloaded inner diameter of the natural vessel, and "$\epsilon$" is a selected value for the strain expected within the natural vessel.

6. A generally tubular extension made in accordance with claim 1 and being attached to a medical device, an opposite end of said tubular extension having a generally elliptical cross-section in a plane perpendicular to said central axis.

* * * * *